(12) United States Patent
Wang et al.

(10) Patent No.: US 8,530,417 B2
(45) Date of Patent: Sep. 10, 2013

(54) Y-SHAPED POLYETHYLENE GLYCOL MODIFIED G-CSF, THE PREPARATION AND USE THEREOF

(75) Inventors: Shiyuan Wang, Fujian (CN); Jianhua Zheng, Fujian (CN); Li Sun, Fujian (CN); Huili Cai, Fujian (CN); Meihua Yang, Fujian (CN); Yan He, Fujian (CN); Ping Chen, Fujian (CN); Hongyuan Deng, Fujian (CN); Liping Zhong, Fujian (CN); Shuying Huang, Fujian (CN)

(73) Assignee: Biosteed Gene Expression Tech Co. Ltd., Fujian (CN)

( * ) Notice: Subject to any disclaimer, the term of this patent is extended or adjusted under 35 U.S.C. 154(b) by 80 days.

(21) Appl. No.: 12/811,103

(22) PCT Filed: Dec. 29, 2007

(86) PCT No.: PCT/CN2007/003897
§ 371 (c)(1),
(2), (4) Date: Jun. 29, 2010

(87) PCT Pub. No.: WO2009/086656
PCT Pub. Date: Jul. 16, 2009

(65) Prior Publication Data
US 2011/0280826 A1 Nov. 17, 2011

(51) Int. Cl.
*A61K 38/00* (2006.01)
*A61K 38/16* (2006.01)
*A61K 38/17* (2006.01)
*A61K 38/24* (2006.01)
*C07K 1/00* (2006.01)
*C07K 16/00* (2006.01)

(52) U.S. Cl.
USPC ....... 514/7.9; 514/19.6; 514/21.2; 514/21.92; 530/402; 530/417; 530/350; 530/399

(58) Field of Classification Search
None
See application file for complete search history.

(56) References Cited

U.S. PATENT DOCUMENTS

| 6,831,158 B2 * | 12/2004 | Nissen et al. | 530/397 |
| 2003/0219404 A1 * | 11/2003 | Yamasaki et al. | 424/85.4 |
| 2005/0180946 A1 * | 8/2005 | Ji et al. | 424/78.38 |

FOREIGN PATENT DOCUMENTS

| CN | 1243779 C | | 3/2006 |
| CN | 1778821 A | | 5/2006 |
| CN | 1778821 W | | 5/2006 |
| WO | 2006094530 A1 | | 9/2006 |
| WO | WO 2006/095029 | * | 9/2006 |
| WO | PCT2007003897 R | | 12/2007 |
| WO | WO 2012/064867 | * | 5/2012 |

OTHER PUBLICATIONS

Kuderer et al. 2006. Cancer 106:2258-2266.*

* cited by examiner

*Primary Examiner* — Shulamith H Shafer
(74) *Attorney, Agent, or Firm* — Millen, White, Zelano & Branigan, P.C.

(57) ABSTRACT

The present invention relates to granulocyte colony stimulating factor (G-CSF) modified with Y-shaped branched polyethylene glycol (YPEG-G-CSF) at a specific lysine (Lys 17) and the preparation thereof, as well as the pharmaceutical composition comprising YPEG-G-CSF and use thereof.

12 Claims, 12 Drawing Sheets

FIGURE 1

The amino acid sequence of G-CSF (SEQ ID NO:1)

MTPLGPASSL PQSFLLKCLE QVRKIQGDGA ALQEKLCATY KLCHPEELVL LGHSLGIPWA PLSSCPSQAL QLAGCLSQLH SGLFLYQGLL QALEGISPEL GPTLDTLQLD VADFATTIWQ QMEELGMAPA LQPTQGAMPA FASAFQRRAG GVLVASHLQS FLEVSYRVLR HLAQP

Separation of YPEG-G-CSF with a cationic ion exchange column

Purification of G-CSF by Sephacryl S-400HR column

Using MALDI-TOF to determine the molecular weight of YPEG-G-CSF

Peptide mass fingerprint mapping on peptide fragments of G-CSF by Maldi-Tof

Peptide mass fingerprint mapping on peptide fragments of PEG-G-CSF by Maldi-Tof

Separation of trypsin-digested G-CSF by RP-HPLC C18 column

Separation of trypsin-digested PEG-G-CSF by RP-HPLC C18 column

The sequencing of the N-terminal amino acid sequence

Assay for the specific biological activity of YPEG-G-CSF

Effect of YPEG-rHuG-CSF on the logarithm value of the number of neutrophils in $^{60}$Co irradiated monkey Comparison of pharmacokinetic curves of PEG-GCSF and G-CSF

SEQUENCE LISTING

```
<160> NUMBER OF SEQ ID NOS: 5

<210> SEQ ID NO 1
<211> LENGTH: 175
<212> TYPE: PRT
<213> ORGANISM: Homo sapiens

<400> SEQUENCE: 1

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
```

```
                        165            170            175

<210> SEQ ID NO 2
<211> LENGTH: 20
<212> TYPE: PRT
<213> ORGANISM: Homo sapiens

<400> SEQUENCE: 2

Met Thr Pro Leu Gly Pro Ala Ser Ser Leu Pro Gln Ser Phe Leu Leu
1               5                   10                  15

Lys Cys Leu Glu
            20

<210> SEQ ID NO 3
<211> LENGTH: 14
<212> TYPE: PRT
<213> ORGANISM: Homo sapiens

<400> SEQUENCE: 3

Gln Val Arg Lys Ile Gln Gly Asp Gly Ala Ala Leu Gln Glu
1               5                   10

<210> SEQ ID NO 4
<211> LENGTH: 13
<212> TYPE: PRT
<213> ORGANISM: Homo sapiens

<400> SEQUENCE: 4

Lys Leu Cys Ala Thr Tyr Lys Leu Cys His Pro Glu Glu
1               5                   10

<210> SEQ ID NO 5
<211> LENGTH: 15
<212> TYPE: PRT
<213> ORGANISM: Homo sapiens

<400> SEQUENCE: 5

Met Thr Pro Leu Gly Pro Ala Ser Ser Leu Pro Gln Ser Phe Leu
1               5                   10                  15
```

Y-SHAPED POLYETHYLENE GLYCOL MODIFIED G-CSF, THE PREPARATION AND USE THEREOF

SEQUENCE LISTING

The instant application contains a Sequence Listing which has been submitted in ASCII format via EFS-Web and is hereby incorporated by reference in its entirety. Said ASCII copy, created on Sep. 30, 2010, is named NTD0010.txt and is 2,820 bytes in size.

FIELD OF THE INVENTION

The present invention relates to granulocyte colony stimulating factor (G-CSF) modified with Y-shaped polyethylene glycol (YPEG-G-CSF) and the preparation thereof, as well as the pharmaceutical composition comprising the same and use thereof.

BACKGROUND OF THE INVENTION

Granulocyte colony stimulating factor (G-CSF) is one of the colony stimulating factors that contribute to the formation of the colonies of bone marrow cells. It can specifically stimulate and regulate the proliferation, differentiation, survival and activation of granulocytes, and is promising in treating granulopenia of various causes.

Human G-CSF gene is located in the q21-22 region on chromosome 17 with a full length of 2.5 kb. The gene is consisted of 5 exons and 4 introns, and the corresponding mature protein comprises 174 amino acids. G-CSF expressed by E. coli has a Met on its N-terminus, and is consisted of 175 amino acids, as shown in FIG. 1 (SEQ ID NO:1). The molecule comprises 5 cystein residues, wherein Cys37-Cys43 and Cys75-Cys85 form two pairs of disulfide bonds, and comprises 4 lysine residues, located on positions 17, 24, 35 and 41 separately.

Neutropenia caused by chemotherapy, especially febril neutropenia (FN) is the most common and usually the most serious side effect after chemotherapy of cancer patients, especially in the first cycle of chemotherapy. FN will lead to enforced hospitalization and use of antibiotics, causing extra economic burden and high fatality. Another damaging result is that due to the reduction of neutrophils, the scheme for the treatment of cancer patients has to be changed, for example reducing the dosage for chemotherapy and postponing the next therapeutic cycle, which are directly related to the final therapeutic result. Since the approval of rHuG-CSF by FDA in 1991, millions of cancer patients subjected to chemotherapy have benefited therefrom. The medicament has been listed as one of top 10 sellers of the world's biotech medicament, and is believed to be very promising.

However, recombinant human G-CSF has shortened in vivo half life ($t_{1/2}$ of about 1.3-4.2 h) and activity, and tends to be hydrolyzed by enzymes and cleared from the kidney, therefore needs to be injected many times, which is very inconvenient for the patient and may cause some undesired responses which will affect the efficacy.

Recently, the development of polyethylene glycol (PEG) modification technique has provided an alternative for solving the above-mentioned technical problem.

PEG is a nontoxic and dissolvable neutral polymer. It is biocompatible and hemocompatible, and has been approved by FDA for tropical and enteral use and intraveneous injection. PEG modification of a protein is achieved by activating one or both terminal groups on both ends of PEG to create a functional group, which is reactive with at least one group in the protein to be bound, so as to bind PEG with the N or C terminal of the protein or a specific amino acid, wherein the site for PEG modification is universal.

PEG is the polymer of ethylene glycol and ethylene oxide, also called carbowax, with the structure shown in the following formula:

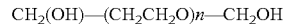

$$CH_2(OH)-(CH_2CH_2O)n-CH_2OH$$

The appearance of conventional PEG changes as its molecular weight increases: it appears from colorless viscous liquid (190-630 Dalton), white paste (950-1050 Dalton) to white waxy or flaky solid (>1200 Dalton). Usually, PEG for modifying proteins or other drugs has a large molecular weight (Table 1), such as the U-shaped double-stranded PEG with a molecular weight of 40 KD employed in Pegasys (PEGylated interferon α2a injection, PEGASYS®, Roche, Shanghai), or the linear PEG with a molecular weight of 12 KD employed in Peg-Intron (PEGylated interferon α2b injection, PEG-INTRON®, Schering-Plough, US), or the linear PEG with a molecular weight of 20 KD employed in Neulasta® (PEGylated granulocyte colony-stimulating factor, Amgen US). The in vivo metabolic process of conjugated PEG is quite clear, indicating that PEG is a good, safe drug modifier with no side effects.

TABLE 1

The parameters for basic physicochemical properties of currently marketed PEGylated protein drugs[18]

| Product (Trade name) | Average MW | MW of PEG | $t_{1/2}$ before pegylation | $t_{1/2}$ after pegylation | Manufacture |
|---|---|---|---|---|---|
| Pegylated L-asparaginase (Oncaspar) | 143 kDa | 5 kDa | 20 h | 2 weeks | Enzon |
| Pegylated IFNα2b (PEGIntron) | 31 kDa | 12 kDa | 4-12 h | 40 h (22-60 h) | Schering |
| Pegylated IFNα2a (Pegasys) | 60 kDa | 40 kDa | 5.1 h (3.7-8.5 h) | 80 h (50-140 h) | Roche |
| Pegylated G-CSF (Neulasta) | 39 kDa | 20 kDa | 3.5 h | 15-80 h | Amgren |

Proteinaceous drugs after polyethylene-glycolation (PEGylation) will have significantly improved properties, including prolonged pharmacokinetic half-life (Table 1), reduced immunogenicity, improved safety, increased efficacy, decreased frequency of administration, increased solubility, enhanced protease resistance, which facilitate the controlled release of the drugs. For example, as disclosed in U.S. Pat. No. 4,179,337, after the conjugation of PEG with enzymes and insulin, the immunogenicity of the proteins is reduced, while a certain percentage of the original activity of the proteins still remains. Another unique effect of pegylation is that the in vitro activity of the protein is decreased, but the in vivo activity is increased. For example, as disclosed in U.S. Pat.

No. 4,179,337, after the conjugation of PEG with an enzyme or insulin, the immunogenicity of the protein is reduced, and the activity of the protein is significantly decreased, but the protein still retains a certain percentage of the original activity.

PEGs used to modify drugs are divided into two types according to the structure: the linear type and the branched type. For example, Pegasys® (PEGylated interferon α2a injection, PEGASYS®, Roche US) employs a U-shaped branched double-stranded PEG derivative, with an average molecular weight ranging from 26 KD-66 KD (U.S. Pat. No. 5,382,657—Filed Aug. 26, 1992—Hoffmann-La Roche Inc.), which is represented by the following formula:

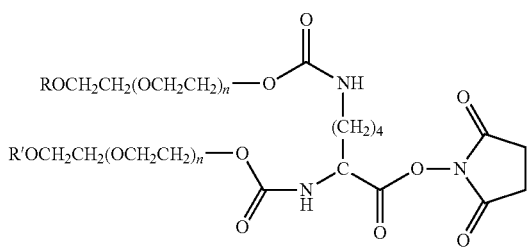

wherein, R and R' are independently low molecular weight alkyl groups, n and n' are from 600 to 1500.

Linear PEG molecule having a molecular weight of 20kD is used in NEULASTA® (pegylated granulocyte colony-stimulating factor, Amgen) approved by U.S. FDA in 2002 (U.S. Pat. No. 5,824,784—Filed Oct. 12, 1994—Amgen Inc.). The reaction for modification is as follows:

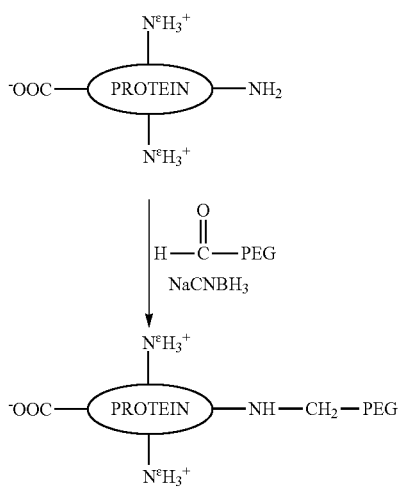

Amgen's Neulasta® employs PEG with aldehyde group on the end. The modification is on the N-terminal amino acid of the protein and PEG-G-CSF modified at a single point is obtained. It is characterized in that PEG is conjugated with G-CSF via C—N bond.

PEGs with different configurations are used, to modify proteins, resulting in products with apparently different features. Prior art literature (Monfardini C, Schiavon O, Caliceti P, et al. Bioconjugate Chem, 1995, 6 (1):62-69) reports that comparing to linear PEG, branched PEG improves the protein's pH resistance, thermal stability and resistance to protease digestion.

Chinese Patent ZL 03801105.0 reported a new double-stranded Y-shaped PEG derivative, which has the following basic structure:

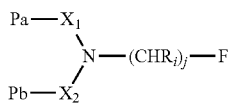

wherein, Pa and Pb are the same or different hydrophilic polymers, which can be polyethylene glycol, polypropylene glycol, polyvinyl alcohol, polyacrylmorpholine or their copolymers, preferably is polyethylene glycol and its copolymers;

j is an integer from 1 to 12;

Ri is H, a substituted or unsubstituted $C_{1-12}$ alkyl group, a substituted aryl, an aralkyl or a heteroalkyl;

$X_1$ and $X_2$ are independently a linking group, wherein $X_1$ is $(CH_2)_n$, and $X_2$ is selected from the group consisting of $(CH_2)_n$, $(CH_2)_nOCO$, $(CH_2)_nNHCO$, and $(CH_2)_nCO$; n is an integer from 1 to 10; and F is a terminal group selected from the group consisting of a hydroxyl group, a carboxyl group, an ester group, acyl chloride, hydrazide, maleimide, pyridine disulfide, capable of reacting with amino, hydroxyl or mercapto group of a therapeutic agent or a protein to form a covalent bond.

When Pa and Pb are preferably PEG or its copolymer, the basic molecular structure thereof is

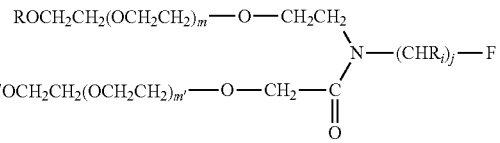

The Y-shaped PEG modifies the protein on the free amino group of the protein, wherein the modification site is not fixed.

In prior art, N-hydroxysuccinimide activation can be used to synthesize Y-shaped branched NHS-PEG which is used for modification. NHS-PEG is characterized in that it can form amide bond with the free amino group on lysine or the free terminal amino group of rhG-CSF, and the amide bond can be hydrolyzed in vivo slowly, so that the activity of rhG-CSF is restored. However, the currently used Y-shaped branched NHS-PEG generally have the defect of high activity and poor selectivity, and cannot be used to achieve directional selection of modification sites, therefore it is difficult to obtain products with modification on a single fixed-site.

SUMMARY OF THE INVENTION

The invention is based on novel Y-shaped PEGylated granulocyte colony stimulating factor (YPEG-G-CSF) with single site modification. Particularly, the invention relates to YPEG modified G-CSF and its preparation method, the pharmaceutical composition comprising YPEG-G-CSF and use thereof. Particularly, YPEG-G-CSF of the present invention is modified on the 17th lysine (K17) as a singe site modification. The use of K17 single site modified YPEG-G-CSF achieves good therapeutic effects in animals. In addition, K17 single site modified YPEG-G-CSF has significantly prolonged pharmacokinetic half-life in serum.

In one aspect, this invention relates to Y-shaped PEG derivatives (also recorded as YPEG) modified G-CSF (also recorded as YPEG-G-CSF or PEG-G-CSF), wherein its molecular composition is as follows

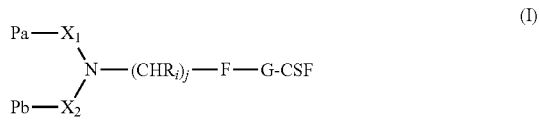
(I)

wherein, Pa and Pb are same or different PEGs;

j is an integer from 1 to 12;

Ri is H, a substituted or unsubstituted $C_1$-$C_{12}$ alkyl group, a substituted aryl, an aralkyl or a heteroalkyl;

$X_1$ and $X_2$ are independently a linking group, wherein $X_1$ is $(CH_2)_n$, and $X_2$ is selected from the group consisting of $(CH_2)_n$, $(CH_2)_n OCO$, $(CH_2)_n NHCO$, and $(CH_2)_n CO$; n is an integer from 1 to 10; and F is a terminal group selected from the group consisting of a hydroxyl group, a carboxyl group, an ester group, acyl chloride, hydrazide, maleimide, pyridine disulfide, capable of reacting with amino, hydroxyl or mercapto group of a therapeutic agent or a substrate to form a covalent bond.

In one embodiment, the structural formula of the Y-shaped PEG-G-CSF has the following structure:

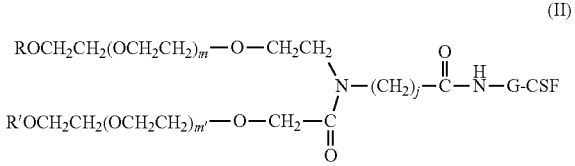
(II)

Wherein R and R' are independently a low molecular weight alkyl, preferably methyl; j is an integer of 1-12; m and m' denote the degree of polymerization and can be any integer; preferably m=m' and m+m' is from 600 to 1500. In formula (II), the Y-shaped branched PEG binds to G-CSF through an amide bond at a single site.

In a preferred embodiment, in said Y-shaped PEG-G-CSF, G-CSF binds Y-PEG through the amide bond formed by the ε-amino group on the side chain of lysine in G-CSF corresponding to position 17 of SEQ ID NO: 1 and the terminal carboxyl group of Y-PEG.

Alternatively, the G-CSF of the present invention can be extracted from natural sources or obtained through recombinant biotechnology. Preferably, G-CSF extracted from natural sources or obtained through recombinant biotechnology is human G-CSF (hG-CSF) shown in SEQ ID NO: 1. More preferably, said human G-CSF is recombinant human G-CSF (rhG-CSF). rhG-CSF can be synthesized, expressed by prokaryotic systems such as *E. coli*, expressed by eukaryotic systems such as *Pichia pastoris*, or expressed by other insect cell systems or mammalian cell systems such as CHO cells. The method for preparation of natural or recombinant G-CSF and the method to detect the activities of G-CSF and its YPEG modified products are conventional to one in the art.

In another aspect, the present invention relates to a method for preparation of YPEG modified G-CSF. In one embodiment, activated derivatives of YPEG such as polyethylene glycol succinimide (YPEG-NHS) shown in formula III can be used to covalently bind PEG with the ε-amino group on lysine corresponding to position 17 in G-CSF through nucleophilic substitution reaction:

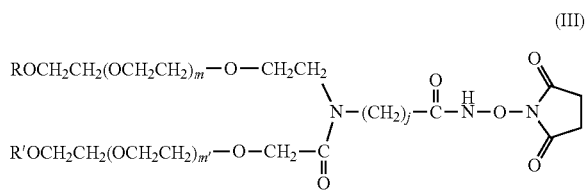
(III)

Wherein, YPEG-NHS can be prepared as described in EP1496076.

The reaction of G-CSF with YPEG to form YPEG-G-CSF is shown as below:

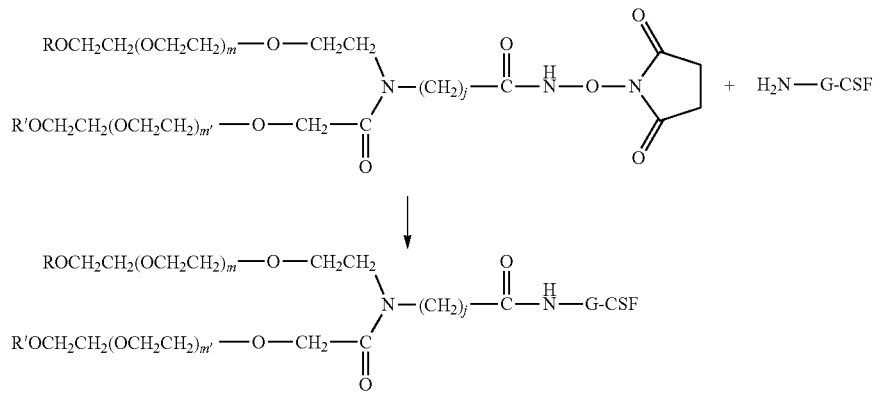

The reaction is performed under mild reaction conditions, pH 6.0-10, preferably 8.0, temperature 0-20° C., mixed by stirring etc. The modification site of pegylation is determined by performing molecular weight analysis on YPEG-G-CSF combined with molecular fingerprint mapping and trypsin digestion pattern and N-terminal sequencing of the protein. The inventor found that the pegylation site on G-CSF was on lysine of position 17, and the product of the modification was recorded as YPEG-G-CSF (17).

The separation and purification of YPEG-G-CSF (17) can be performed by methods such as ion exchange. In one embodiment, the prepared YPEG-G-CSF is passed through a cationic ion exchange column, the fourth active peak is collected, and the product is further purified by a Sephacryl S-400HR column to obtain the purified YPEG-G-CSF (17).

The invention also provides the use of the YPEG-G-CSF of the present invention or the composition comprising the YPEG-G-CSF of the present invention in treating disease in need of G-CSF treatment. The clinical use of the pegylated G-CSF or the composition comprising the pegylated G-CSF of the present invention is the same as that of G-CSF, and they all can be applied in treating granulocytopenia-related diseases such as granulocytopenia induced by severe infection, treatment for leukemia, stem cell transplantation, and malignant solid tumor chemotherapy (Ying Tong et. al, "The clinical application of G-CSF and GM-CSF", Basic & Clinical Medicine 2000 Vol. 20 No. 2 P. 101-104). In vivo results show that compared with G-CSF, the use of YPEG-G-CSF of the present invention achieves unexpected effects—the same or better efficacy is achieved even if the total dosage is reduced, see the working examples. In addition, the pharmacokinetic half life of YPEG-G-CSF of the present invention in serum and other properties are significantly improved. The YPEG-G-CSF of the invention can be administered to patients in the form of composition, wherein the composition contains a pharmaceutically effective amount of YPEG-G-CSF and a pharmaceutically acceptable carrier or excipient. Preferably, the above composition contains mannitol, amino acids, sodium acetate and acetic acid, wherein the amino acid is selected from aspartic acid, asparagine and glycine. The composition can be prepared into appropriate dosage forms, and administered by experienced physicians in any acceptable suitable manner. The invention also provides a method for treatment of neutropenia, which include the administration of the composition comprising YPEG-G-CSF of the present invention.

BRIEF DESCRIPTION OF THE DRAWINGS

FIG. 1: shows the amino acid sequence of G-CSF (SEQ ID NO:1), MW18801.79, PI 5.62, wherein the underlined amino acids represent five theoretical sites for modification by YPEG in the amino acid sequence, including N-terminal amino group and the free amino group on Lys.

DETAILED DESCRIPTION OF THE INVENTION

The present invention will be further illustrated by the following examples. The advantages of the present invention compared to prior art are:

1. YPEG-G-CSF of the present invention is obtained by using YPEG to modify G-CSF and purifying the reaction mixture to obtain products with single site modification on $K^{17}$, so as to solve the following technical problem to facilitate quality control and to ensure batch-to-batch stability in mass production: since NHS-PEG has high activity, poor selectivity, and cannot be used for directional selecting of the modification site, it is difficult to obtain products with a single site modified.

2. The in vivo circulating half-life of YPEG-G-CSF of the present invention is significantly prolonged compared to G-CSF.

3. YPEG-G-CSF of the present invention significantly improves in its phaacodynamical features compared with non-pegylated G-CSF. Particularly, when using the same amount or even smaller amount of YPEG-G-CSF compared to conventional G-CSF, the former can achieve the same or even more obvious therapeutic effects.

One in the art should understand that any examples or their combination should not be understood as limiting the scope of the present invention. The scope of the present invention is defined by the accompanying claims, and a person of ordinary skill can clearly understand the scope defined by the claims combined with the teaching of the description and common sense.

EXAMPLES

Example 1

Preparation of YPEG-G-CSF

Figure 2:
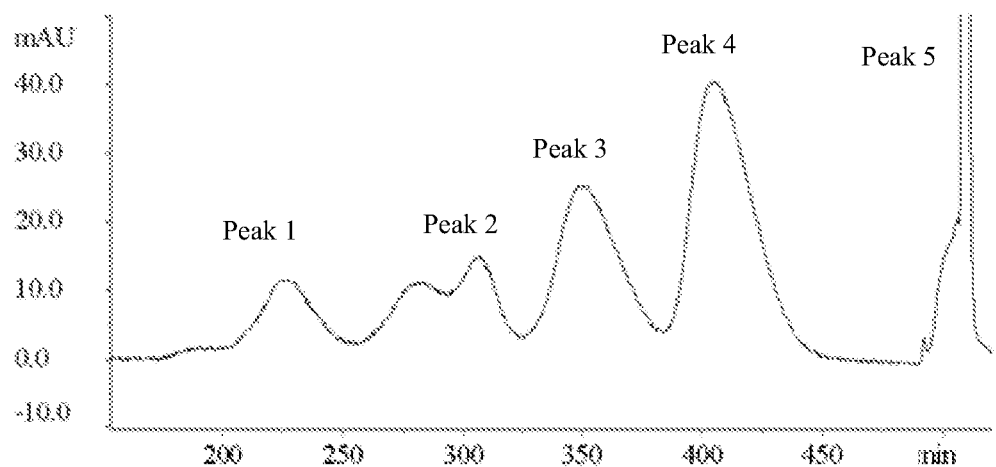
FIG. 2 shows the peaks obtained from separation of YPEG-G-CSF by a cationic ion exchange column, wherein the fourth (4#) peak is the target peak of YPEG-G-CSF (17).
Figure 3:
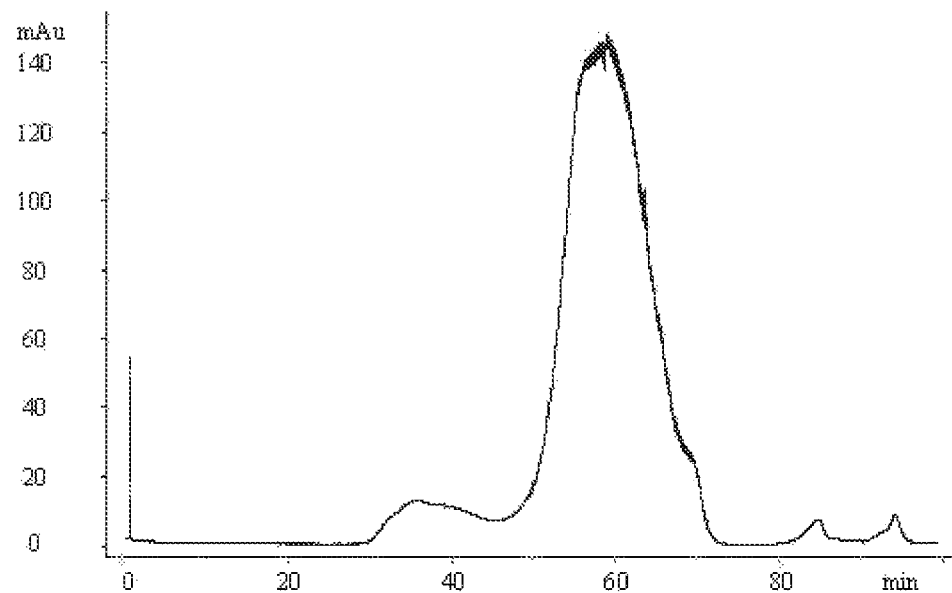
FIG. 3 shows the peak obtained from purification of YPEG-G-CSF by use of Sephacryl S-400HR column.

The stock buffer system containing 400 mg G-CSF at a concentration of 9.58 mg/ml was replaced by 50 mM sodium borate buffer (pH8.0), and 2 mM HCl was used to dissolve 3.2 g 40 KD NHS-YPEG (purchased from Beijing JianKai Technology Co., Ltd.). The protein and PEG were mixed at the ratio of protein: PEG=1:6 (mass ratio). The mixture was maintained at 4° C. for 3 hours, and then diluted 15 times with 10 mM NaAc pH4.0 before loaded on a cationic ion exchange column (purchased from GE Healthcare) equilibrated with 10 mM NaAc/HAc pH4.0. 10 mM NaAc/HAc+NaCl 160 mM pH4.0 gradient elution buffer was used to elute the diluted mixture, and the fourth active peak was collected (FIG. 2). Sephacryl S-400HR column (purchased from GE Corporation) equilibrated with 10 mM sodium phosphate buffer (pH7.0) was used to remove the macromolecular polymers, and the active peak was collected (FIG. 3). 10 mM NaAc pH4.0 buffer system was used for ultrafiltration, and 73 mg sample was obtained.

Example 2

Determination of the Molecular Weight of PEG-G-CSF

MALDI-TOF was used to determine the molecular weight of the PEG-G-CSF obtained in Example 1. Particularly autoflex TOF/TOF mass spectrometry (Bruker Daltonics, Germany) and the TOF/TOF MS method were used to determine the molecular weight of YPEG-rHuG-CSF and rHuG-CSF. Matrix used is sinapinic acid (SA, $C_{11}H_{12}O_5$, MW 224.22), and the analysis software is the flexAnalysis Ver.3.0.54.0.

Figure 4:
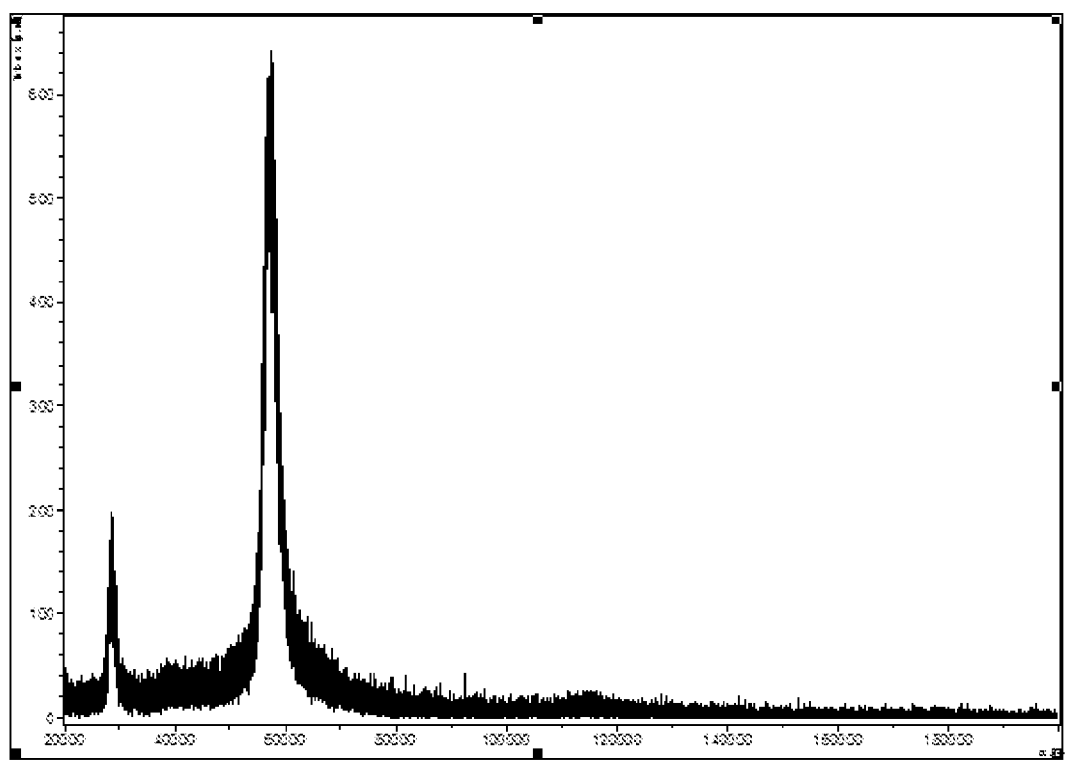
FIG. 4 shows the result obtained by using MALDI-TOF to determine the molecular weight of YPEG-G-CSF.

Test results: The MS molecular weight of YPEG-rHuG-CSF was about 59 kD, consistent with the theoretical molecular weight 58801.8 Dalton. The result was shown in FIG. 4.

YPEG-rHuG-CSF was obtained by modifying rHuG-CSF with YPEG. Modifier (YPEG) was the mixture of a series YPEGs whose molecular weights were normally distributed, with an average molecular weight of 40 kD±10%. Due to the normal distribution of the molecular weight of YPEG, the molecular weights of YPEG modified products were also normally distributed (±10%), i.e. the molecular weight of YPEG-rHuG-CSF should be 58802.0 Dalton ±10%.

Example 3

Determination of the Pegylation Site

The pegylation site in PEG-G-CSF obtained from Example 1 was analyzed.

Figure 5:
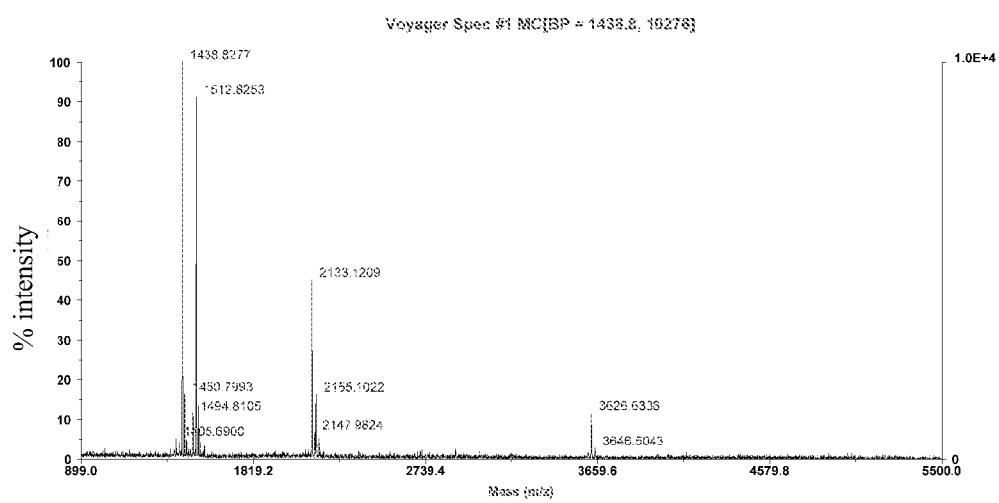
FIG. 5 shows the result obtained by using Maldi-Tof to perform peptide mass fingerprint mapping on peptide fragments of G-CSF.
Figure 6:
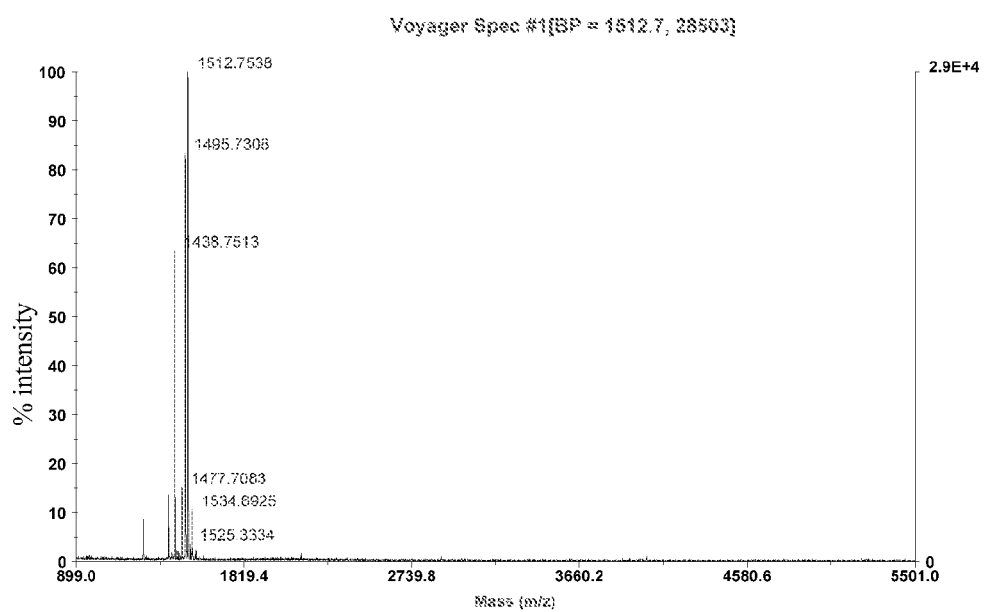
FIG. 6 shows the result obtained by using Maldi-Tof to perform peptide mass fingerprint mapping on peptide fragments of PEG-G-CSF.

The buffer containing G-CSF and PEG-G-CSF was replace by 50 mM $(NH_4)HCO_3$, pH8.0. Endoproeinase Glu-C was added in the ratio of 1:20 to digest YPEG-G-CSF, and the Maldi-Tof method was used to perform peptide mass fingerprint mapping on the obtained peptide fragments. The results were shown in FIG. 5 and FIG. 6.

The above results indicated that, the following peptide fragments could be obtained from G-CSF/Glu-C: peptide fragments of 1-20 amino acids, which contained the YPEG reaction sites $M^1$ and $K^{17}$ (MTPLGPASSLPQSFLLKCLE, molecular weight 2132.6D) (SEQ ID NO: 2), peptide fragments of 21-34 amino acids, which contained YPEG reaction site $K^{24}$ (QVRKIQGDGAALQE, molecular weight 1512.7D) (SEQ ID NO: 3), peptide fragments of 35-47 amino acids, which contained YPEG reaction sites $K^{35}$ and $K^{41}$ (KLCATYKLCHPEE, molecular weight 1534.7D) (SEQ ID NO: 4). Peptide fragment of 1-20 amino acids could not be obtained from YPEG-G-CSF/Glu-c, but peptide fragments of 21-34 amino acids (QVRKIQGDGAALQE) (SEQ ID NO: 3) and of 35-47 amino acids (KLCATYKLCHPEE) (SEQ ID NO: 4) were obtained, indicating that the modification did not occur at $K^{24}$, $K^{35}$ and $K^4$, but in the N-terminal amino acid or lysine at position 17, resulting in the change of the molecular weight of the peptide fragment compared with the unmodified peptides due to the conjugation with YPEG of 40kD.

To confirm this conclusion, the inventor compared the mapping of PEG-G-CSF with that of G-CSF. Sequencing grade trypsin (Promega, swine, seq. grade modified, >5000 U/mg) was diluted with a buffer solution to the concentration of 1 μg/ul. G-CSF-PEG was subjected to ultra-filtration, and the buffer was replaced with 50 mM $NH_4HCO_3$ pH8.0 so that sample solution with the concentration of PEG-G-CSF of 1 mg/ml was obtained. Adding 1 μl trypsin into 50 μl YPEG-G-CSF sample, and incubating the mixture at 37° C. for 24 hours. The unmodified G-CSF sample was treated in the same way as control.

Figure 7:
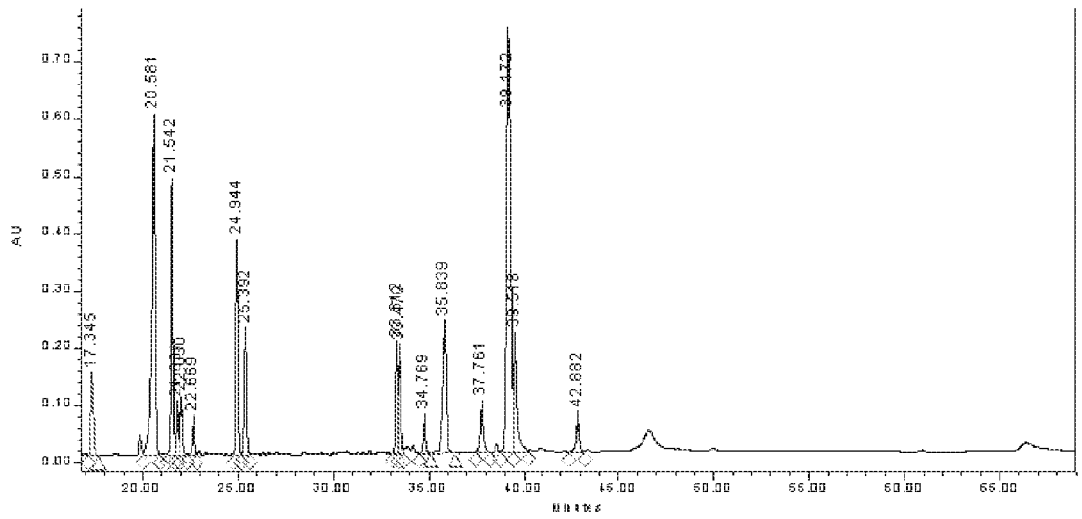
FIG. 7 shows separation of trypsin-digested G-CSF by RP-HPLC C18 column.
Figure 8:
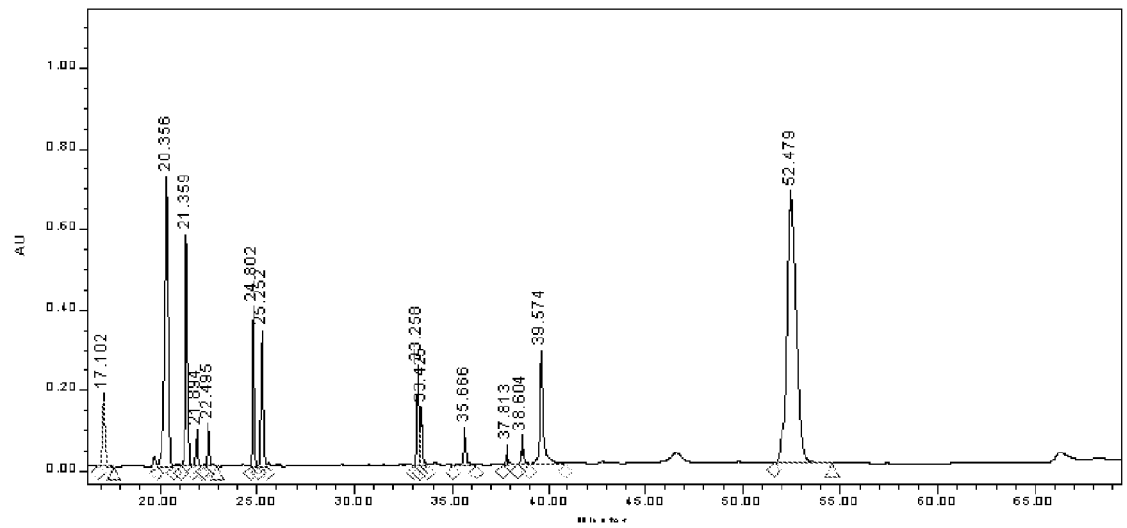
FIG. 8 shows separation of trypsin-digested PEG-G-CSF by RP-HPLC C18 column.

Digested G-CSF and PEG-G-CSF samples were separated by C18 RP-HPLC column filled with octadecylsilyl (Φ4.6 mm×150 mm, particle diameter 5 μm, pore size 300 Å). Gradient elution was performed under the following conditions: mobile phase A 0.1% $TFA/H_2O(V/V)$, mobile phase B 0.1% TFA/90% ACN (V/V); flow rate 1.0 ml/min, as shown in Table 2. The result was shown in FIG. 7 and FIG. 8.

TABLE 2

Elution gradients on HPLC-RPC C18 for mapping of digested YPEG-rHuG-CSF

| time (min) | A % | B % |
|---|---|---|
| 1 | 0 | 100 | 0 |
| 2 | 1 | 100 | 0 |
| 3 | 71 | 30 | 70 |
| 4 | 81 | 0 | 100 |
| 5 | 91 | 100 | 0 |
| 6 | 100 | 100 | 0 |

Compared with the unmodified G-CSF, the peptide mapping of PEG-G-CSF showed an additional peak at 52.479 min but the peak at 39.172 min disappeared. The peptide fragments were collected and the five N-terminal amino acids were subjected to Edman degradation. The result showed that all the peptide fragments had the same N-terminal sequence MTPLG. The retention time of the peptide fragments changed after conjugation with YPEG, indicating that the YPEGylation site indeed occurred at the N-terminal segment.

Figure 9:
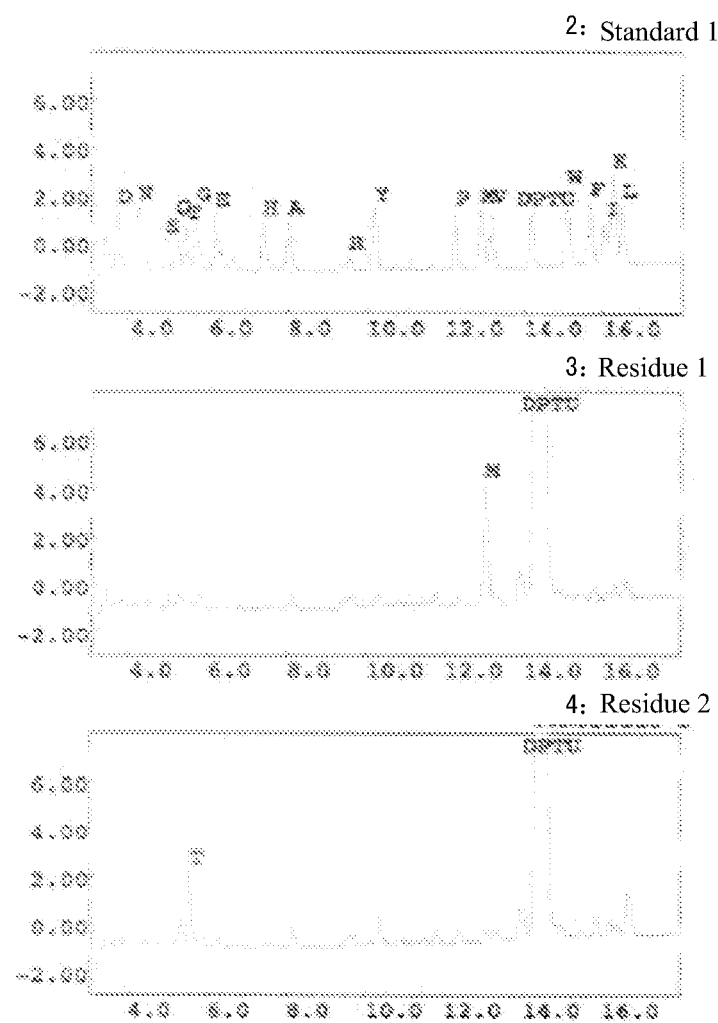
FIG. 9 shows the sequencing of N-terminal amino acid sequence of YPEG-G-CSF.

The PEG-G-CSF was further subjected to N terminal sequencing, and was found to have the N terminal 15 amino acid sequence MTPLGPASSLPQSFL (SEQ ID NO: 5). Analysis showed that the first amino acid was the Met, and compared to the second amino acid Thr, its peak area was not significantly reduced (FIG. 9), indicating the existence of free amino group on the N terminus, which was not modified. That is to say PEG modification did not occur on the N terminal M1, but on K17. The result proved that the YPEG-G-CSF prepared in Example 1 was modified on the single site of K17.

Example 4

Assay of the Biological Activity of PEG-G-CSF

1. Formulation of Agents and Cell Cultivation 1.1 1640 medium: RPMI1640 liquid medium, which was incubated at 4° C.; or which was formulated according to the instructions of the manufacture. Penicillin and streptomycin were added into the medium to 105 IU/L before use.

1.2. Minimal culture medium: 1640 solution with 2.5% fetal bovine serum (FBS, v/v) and 12.5% horse serum (ES, v/v), incubated at 4° C.

1.3 Complete culture medium: rhG-CSF was added into minimal culture medium to a final concentration of 20 ng (2000 U)/ml, 4° C.

1.4 NFS-60 cell line: The cells were cultivated in complete culture medium at 37° C., 5% $CO_2$ and passaged every 48 to 72 hours. The concentration of the cells was controlled between $2.0×10^5$-$10.0×10^5$/ml. The titer of rhG-CSF was determined 24-36 hours after the last passage.

1.5 Phosphate buffer (Hyclone): 8 g NaCl, 0.2 g KCl, 1.44 g disodium hydrogen phosphate, 0.24 g of potassium dihydrogen phosphate were formulated into 1000 ml solution with ultra-pure water. After 121° C., 15 min of incubation the solution was autoclaved.

1.6 MTT solution: MTT powder (Sigma) was formulated with phosphate buffer solution into 5.0 mg/ml, and sterilized by 0.22 μm membrane filter, stored at 4° C. in dark. 1.7 lysis buffer Lysis buffer 1: Isopropyl alcohol solution containing 1% concentrated HCL, 5% TritonX-100, stored at room temperature in dark.

Or lysis buffer 2: Isopropyl alcohol solution containing 2.8% concentrated HCL, 10% TritonX-100, stored at room temperature in dark.

2. Assay of the Biological Activity of PEG-G-CSF 2.1 Preparation of cell suspension Enough amount of NFS-60 cell culture was centrifugated to collect NFS-60 cells. The collected cells were washed with PBS 3 times, and then resuspended in minimal culture medium. The cell concentration was adjusted to about $2.0 \times 10^5$/ml, preserved at 37° C.

2.2 G-CSF standard (working standard, or national standard provided by NICPBP, with the international standard used as a reference for check) and the samples to be tested were prediluted to 2 ng/ml by minimal culture medium according to the amount of protein, and the dilution factor for each step was no more than 10.

2.3 Minimal culture medium was added into the 96 cell plate at 50 µl/well. The reference materials and samples to be tested obtained in 2.2 were serially diluted at 1:2 to eight different concentrations of 1 ng/ml, 0.5 ng/ml, 0.25 ng/ml . . . , and each well contained 50 µl. Negative control (without rhG-CSF) and positive control (with rhG-CSF 2 ng/ml) were set, each in at least triplicate.

2.4 50 µl cell suspension per well was added, and incubated at 37° C., 5% $CO_2$ for 40-48 hours. After a substantive number of the negative cells (>95%) were disrupted, MTT solution was added at 20 µl per well, incubated at 37° C., with 5% $CO_2$ for 4-6 hours.

2.5 180 µl lysis buffer 1 or 100 µl lysis buffer 2 was added into each well, mixed and assayed by colorimetric method at wavelength of 570 nm, and the reference wavelength was 630 nm.

3. Result

The dose-effect relationship of the standard and the sample to be tested was plotted with OD570 nm-630 nm value as Y axis and the logarithmic values of the dilution gradient on the plate as X-axis. Test data were processed by four factor fitting method. The $ED_{50}$ (50% effective dose) value at OD570 nm-630 nm was calculated as the mean value of the maximum drug concentration and the minimum drug concentration on the curve of the standard at OD570 nm-630 nm. The logarithm value of the dilution factor corresponding to ED50 at OD570 nm-630 nm on the sample curve was defined as the C value of the sample. The calculation was performed according to the following equation:

Titer of Sample to be tested (IU/vial)=titer of the standard$\times C1/C2 \times D1/D2 \times V$ Wherein: C1 is the dilution factor of the sample corresponding to ED50 of the standard;

C2 is the dilution factor of the standard at ED50;

D1 is the pre-dilution factor of sample to be tested;

D2 is the pre-dilution factor of the standard;

V is labelled volume of the vial (expressed in ml).

Figure 10:
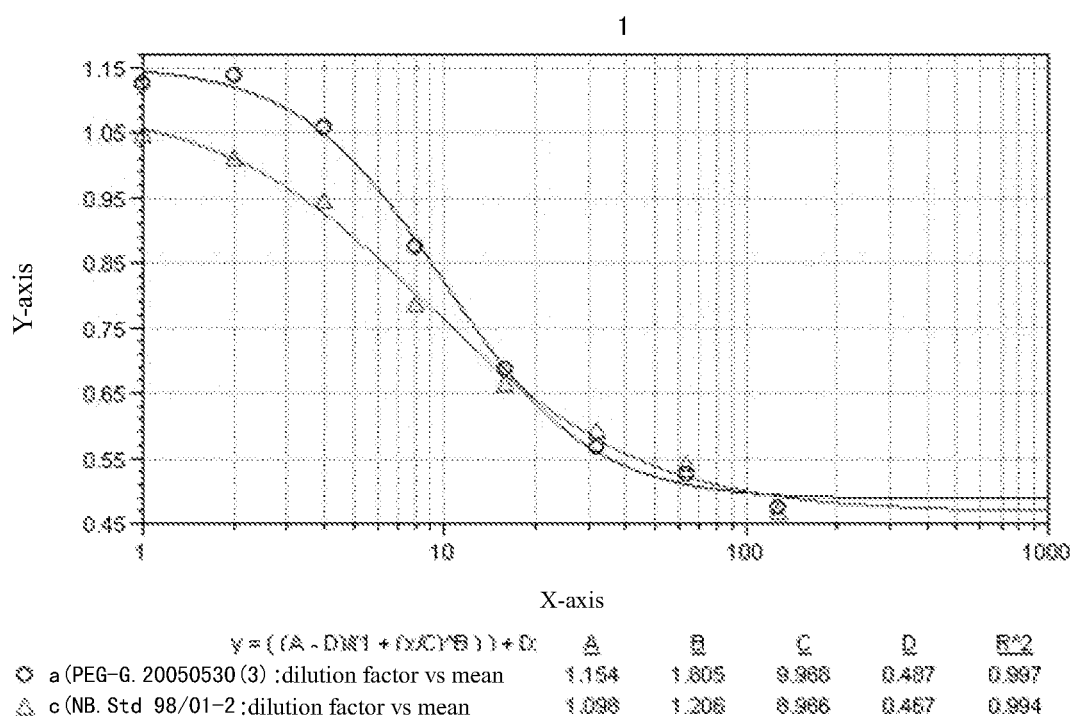
FIG. 10 shows the result of the assay for the specific biological activity of YPEG-G-CSF.

It was determined that the biological activity of YPEG-G-CSF prepared in the working Examples was $2.96 \times 10^7$ IU/mg (FIG. 10).

Example 5

Pharmacodynamic Assay of YPEG-G-CSF (A) Effect of the Pegylated Granulocyte Colony Stimulating Factor (YPEG-G-CSF) on 5-Fluorouracil Induced Granulocytopenia 1. Materials and Methods The test sample: YPEG-G-CSF standard (Biosteed Gene Expression Tech Co. Ltd.): 1 mg/vial, stored at 2-8° C.

Positive control: Filgrastim (rhG-CSF) 300 µg/vial (KKPHARM Co. Ltd), stored at 2~8° C. in dark.

Animals: 140 male mice (Kunming, SPF grade, Staidson Pharmaceutical Co., Ltd. Beijing, license number SCXK-(Beijing)-2006-0004). The mice were randomly divided into 7 groups: the normal control group, model control group, low dose group 1, low dose Group 2, medium dose group and high dose group and the positive control group.

Modelling approach: Except for the normal control group, the model control group and each treatment group received a dose of 150 mg/kg of 5-FU, and were subjected to therapy with the test sample or control the next day.

Dosage and Frequency:

YPEG-rHuG-CSF was administered at a dosage of 15, 50, 150, 500 µg/kg, every 4 days, for 3 times. The dosage of the positive control was 50 µg/kg, administered every 1-11 days. The schedule was shown in Table 3.

TABLE 3

YPEG-rHuG-CSF dose design

| | Group | Dosage µg/kg | Modelling | Frequency |
|---|---|---|---|---|
| Normal control | | 0 | — | — |
| Model control | | 0 | 5-FU, iv, 150 mg/kg | — |
| Low dose 1 | YPEG-rHuG-CSF-1 | 15 | 5-FU, iv, 150 mg/kg | d1, d5, d9 |
| Low dose 2 | YPEG-rHuG-CSF-2 | 50 | 5-FU, iv, 150 mg/kg | d1, d5, d9 |
| Medium dose | YPEG-rHuG-CSF-3 | 150 | 5-FU, iv, 150 mg/kg | d1, d5, d9 |
| High dose | YPEG-rHuG-CSF-4 | 500 | 5-FU, iv, 150 mg/kg | d1, d5, d9 |
| Positive control | G-CSF | 50 | 5-FU, iv, 150 mg/kg | d1-d11 |

Administration:

Except for the normal control group and the model control group, other groups were administered subcutaneously with the test sample and positive control 24 hours after administration for modeling at the given frequency.

2. Result

The number of neutrophils in mice was reduced in response to 5-FU, and after 3-9 days the number of neutrophils in most animals was too low to be detected. The percentages of neutrophils before test, and 3 and 9 days after the test were determined, and the absolute neutrophil count (ANC) was calculated. The results were shown in Table 4. The results showed that after the administration of 5-FU, ANCs of model control group and the 15 µg/kg group were significantly reduced on day 3 ($p<0.05$ and $p<0.01$ compared to the normal control group), while the ANCs of the 50-500 µg/kg group and the positive control group were not reduced compared to the number of WBC in control groups. The results indicated that the test sample of 50-500 µg/kg could slow down the reduction of ANC. To day 9, ANC of the model group was still lower than that of normal control, while the ANC of the 150 and 500 µg/kg group was higher than the level of the normal control group, and the ANC of the positive control group also reached that of the normal control group. The ANC level of the model control group at 11 day reached the level of the normal control group, indicating that the test sample or positive control could increase animal neutrophils to normal levels sooner.

TABLE 4

Effect of YPEG-rHuG-CSF on 5-FU mice ANC (×10⁹/L)

| Group | time | | |
|---|---|---|---|
| | D0 (n = 20) | D3 (n = 10) | D9 (n = 10) |
| Normal control | 3.73 ± 1.23 | 5.73 ± 1.88 | 3.81 ± 1.26 |
| Model control | 3.13 ± 0.97 | 3.25 ± 1.43▲ | 1.78 ± 0.68▲ |
| Low dose 1 | 4.53 ± 2.14 | 2.74 ± 1.06▲▲ | 2.59 ± 1.30 |
| Low dose 2 | 4.72 ± 3.87 | 3.90 ± 1.82 | 3.00 ± 0.96* |
| Medium dose | 3.96 ± 1.21 | 4.63 ± 1.70 | 7.80 ± 2.42**▲▲ |
| High dose | 4.34 ± 1.59 | 4.87 ± 2.13 | 12.81 ± 6.15**▲▲ |
| Positive control | 4.23 ± 1.79 | 4.97 ± 1.20** | 4.84 ± 3.10 |

YPEG-rHuG-CSF on 5-FU in mice ANC (×10⁹/L)

| Group | Time | | |
|---|---|---|---|
| | D10 (n = 10) | D11 (n = 10) | D12 (n = 10) |
| Normal control | 4.99 ± 2.13 | 5.26 ± 1.19 | 5.23 ± 1.22 |
| Model control | 2.24 ± 0.92▲ | 5.48 ± 3.17 | 5.73 ± 2.23 |
| Low dose 1 | 10.35 ± 2.87**▲▲ | 7.92 ± 2.91**▲▲ | 5.62 ± 2.31▲▲ |
| Low dose 2 | 15.71 ± 7.15**▲▲ | 23.60 ± 7.39**▲▲ | 8.47 ± 3.45**▲▲ |
| Medium dose | 33.07 ± 11.42**▲▲ | 44.41 ± 16.28**▲▲ | 21.02 ± 7.90**▲▲ |
| High dose | 32.80 ± 16.74**▲▲ | 52.67 ± 16.17**▲▲ | 41.08 ± 23.71**▲▲ |
| Positive control | 9.72 ± 3.66**▲▲ | 9.56 ± 6.40 | 24.21 ± 7.20**▲▲ |

The values shown in the table is $\bar{x} \pm$ SD. n represents for the number of animals, but the actual number of animals in which the number of neutrophils was measurable is less than n.
Compared with the model group, **$P < 0.01$; *$P < 0.05$; with the normal control group, ▲▲$P < 0.01$; ▲$P < 0.05$.

3. Conclusion

The inventor found that besides the significant long-lasting effect, YPEG-G-CSF demonstrated significant protection against 5-fluorouracil induced neutropenia in mice. YPEG-G-CSF could shorten the course of neutropenia in neutropenia mouse model, so that the number of peripheral blood neutrophils could be recovered at an accelerated rate. Comparing G-CSF administered once a day at 50 μg/kg for 11 time (Filgrastim 50 μg/kg×11) to YPEG-G-CSF 50 μ/kg administered every 4 days for 3 times (low dose YPEG-G-CSF 50 μg/kg×3, medium dose CSF 50 μg/kg×3), it was apparent that although the total dosage of YPEG-G-CSF of the present invention was significantly reduced, its effect on increasing the number of neutrophils was equivalent or much better.

(B) The Therapeutic Effect of Y-Shaped PEG Modified Recombinant Human Granulocyte Colony-Stimulating Factor (YPEG-rHuG-CSF) on $^{60}$Co 3.0 Gy Radiation-Induced Neutropenia in the Monkey

1. Materials and Methods

Test sample: YPEG-G-CSF (Biosteed Gene Expression Tech Co. Ltd.): 1 mg/vial, stored at 2-8° C.

Positive control: Filgrastim (rhG-CSF) 300 μg/vial (KKP-HARM Co. Ltd), stored at 2~8° C., dark.

Experimental animals: Cynomolgus monkeys, male and female, 3-4 years old, weight 2.5-4.5 kg (Xishanzhongke Laboratory Animal Co., Ltd., Su Zhou, License No.: SCXK (Su) 2002-0032). Model control group comprised 5 animals, the other groups comprised 4 animals each.

Modelling and administration: After 30 days of quarantine and adaptative feeding, animals were irradiated with $^{60}$Co at 3.0 Gy on whole body, radiation dose rate 1.8 Gy/min. Animals were administered on the day of exposure (in 5 hours) subcutaneously on the inside of hind limbs. See Table 5 below.

TABLE 5

Dosage regimen design

| Group | Dosage (μg/kg) | Number of animals | Frequency |
|---|---|---|---|
| Normal control | — | 6 | — |
| Model control | — | 5 | — |
| Test sample | 25 | 4 | Once every 6 days, d0, d6, d12, d18, d24 |
| Positive control | 10 | 4 | Once per day, d0-d24 |

2. Analysis of the Results

Figure 11:
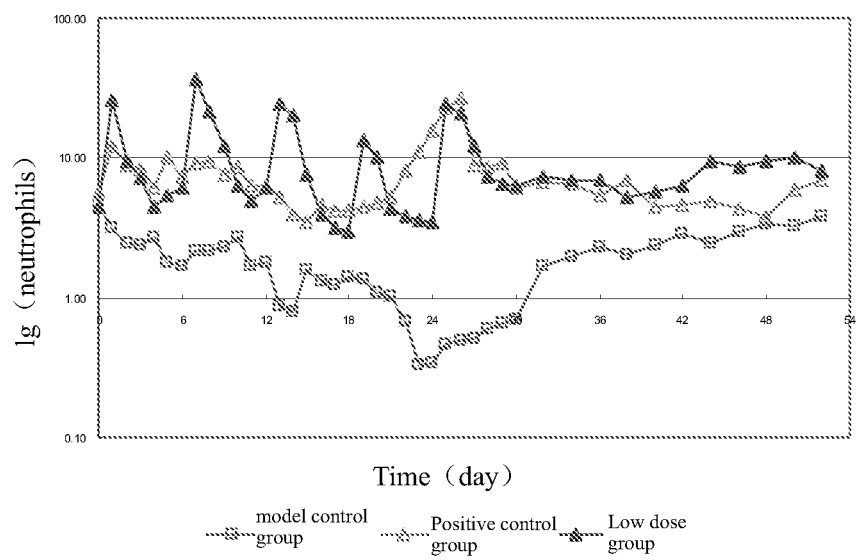
FIG. 11 shows the effect of YPEG-rHuG-CSF on the logarithm value of the number of neutrophils in $^{60}$Co irradiated monkey.

During the test, blood parameters were measured every day, and the number of neutrophils was counted. The results showed that, in low, medium and high dose groups and the positive control group, the mean ANCs were higher than that in model control group, and comparison between dose groups and model control group at different time points showed significant differences ($p<0.05$ or $p<0.01$). The results were shown in Table 6, FIG. 11.

TABLE 6

YPEG-rHuG-CSF on ANC of $^{60}$Co irradiated monkey (×10$^9$/L)

| group | time | | | |
|---|---|---|---|---|
| | D0 | D3 | D6 | D9 |
| Model control | 5.94 ± 1.88 | 2.40 ± 0.95 | 1.67 ± 0.57 | 2.30 ± 0.87 |
| Positive control | 5.62 ± 2.68 | 8.37 ± 3.78* | 7.44 ± 2.67** | 7.71 ± 1.40** |
| Test sample | 4.52 ± 0.85 | 7.15 ± 2.24** | 6.04 ± 1.28** | 12.31 ± 5.33** |

| group | time | | | |
|---|---|---|---|---|
| | D12 | D15 | D18 | D21 |
| Model control | 1.78 ± 1.13 | 1.58 ± 0.71 | 1.41 ± 0.91 | 1.01 ± 1.03 |
| Positive control | 6.40 ± 2.43* | 3.44 ± 1.12* | 4.26 ± 1.36* | 5.24 ± 3.77* |
| Test sample | 6.60 ± 2.59* | 7.52 ± 4.91* | 3.00 ± 0.87* | 4.36 ± 2.11* |

| group | time | | | |
|---|---|---|---|---|
| | D25 | D28 | D30 | D34 |
| Model control | 0.46 ± 0.36 | 0.59 ± 0.28 | 0.69 ± 0.25 | 1.96 ± 1.35 |
| Positive control | 22.58 ± 20.07* | 8.76 ± 7.91 | 6.19 ± 4.15* | 6.50 ± 3.33* |
| Test sample | 24.68 ± 13.79* | 7.30 ± 2.98** | 6.28 ± 3.80* | 6.98 ± 3.79* |

| group | time | | | |
|---|---|---|---|---|
| | D38 | D42 | D46 | D50 |
| Model control | 2.05 ± 1.16 | 2.90 ± 0.92 | 3.00 ± 0.91 | 3.22 ± 0.51 |
| Positive control | 6.84 ± 2.80* | 4.56 ± 1.52 | 4.32 ± 1.34 | 5.94 ± 3.12 |
| Test sample | 5.29 ± 3.03 | 10.19 ± 5.65* | 8.62 ± 3.61* | 10.14 ± 9.80 |

The values shown in the table was $\bar{x}$ ± SD. Model control group included 5 mice, and other groups comprised 4 mice. Compared to model control group, **P < 0.01; *P < 0.05.

3. Conclusion

Y-PEGylated recombinant human granulocyte colony-stimulating factor (YPEG-rHuG-CSF) exerted therapeutic effects on radiation-induced neutropenia of cynomolgus monkey.

YPEG-rHuG-CSF had a prolonged effect in vivo. The above results showed that, compared with injection of 10 μg/kg G-CSF once per day for 25 times, injection of 25 μg/kg YPEG-G-CSF of the invention once every 6 days for 5 times achieved equivalent stimulating effects on neutrophils with less amount of drug.

Example 6

In Vivo Pharmacokinetic Assay for YPEG-G-CSF

1. Methods and Procedures 1.1 Drugs and Reagents

Test sample: YPEG-G-CSF standard (Biosteed. Gene Expression Tech Co. Ltd.): 1 mg/per injection, stored at 2-8° C.

Positive control: Filgrastim(rhG-CSF) 300 μg/vial (KKP-HARM Co. Ltd), stored at 2~8° C. in dark.

1.2 Animals

6 Cynomolgus monkeys, 3 males and 3 females. (Monkey Forest Management and Development Center of Guangxi feeding base production (certificate number: SCXK (Gui) 2005-0005)), weight 3.11~5.62 kg, subjected to sub-caged feeding with standard monkey feed. Water was provided ad lib. and fresh fruit was provided twice a day.

1.3 Experiment Design

The experiment included 2 groups, YPEG-G-CSF of 300 μg/kg subcutaneously, G-CSF(Filgrastim) 300 μg/kg.

2. Experimental Methods 2.1 Blood Sampling

YPEG-rHuG-CSF was injected subcutaneously once before administration, or 0.25 h, 0.5 h, 1 h, 2 h, 4 h, 8 h, 24 h, 48 h, 96 h, 168 h, 240 h, 312 h, 384 h and 480 h after administration and 1 mL venous blood was taken from the opposite hind limb. For the Filgrastim (G-CSF) group, 1 mL venous blood was taken before administration or 5 min, 15 min, 30 min, 1 h, 2 h, 4 h, 8 h, 12 h, 24 h after administration. The blood samples were incubated 4° C. for 30 min, then subjected to 3000 rpm low speed centrifugation for 10 min, and serum was immediately separated and stored at −20° C. until analysis.

2.2 Assay of Serum Drug Concentration

Immunohistochemical Assay Kit (ELISA) was used for determining serum G-CSF or YPEG-rHuG-CSF concentrations in cynomolgus monkeys. Human G-CSF ELISA kit (Ray Biotech Inc.) was used in ELISA for the determining serum G-CSF and YPEG-rHuG-CSF concentrations.

2.2.1 Principle of the Assay

The analysis was based on quantitative sandwich technique. Monoclonal antibodies against recombinant human G-CSF were pre-coated on the microplate. The standard and the samples were transferred into the wells, wherein G-CSF or YPEG-G-CSF would bind the immobilized antibodies. All unconjugated materials were washed off, and anti-human G-CSF IgG conjugated with horseradish peroxidase (HRP) was added into the wells. After washing off all the unconjugated antibody-enzyme reagents, the color produced after addition of the substrate for HRP was proportional to the amount of the conjugated G-CSF or YPEG-G-CSF. Stop the reaction to determine the intensity of color. The concentration of G-CSF or YPEG-G-CSF in the sample increased with the OD value.

2.2.2 Procedures of the Assay

The assay was operated according to the instructions in the kit. 100 μL standard or serum samples were added into each well and mixed gently. According to the expected concentration of the samples, the mixture is diluted into the range of standard calibration curve. Standard calibration curve for recombinant G-CSF or YPEG-G-CSF were set for each plate to calculate the concentration of the unknown samples. The mixture was incubated at room temperature for 1 h. The plate was washed 3 times, and 100 μL second antibody was added into each well, and incubated at room temperature for 1 h. The plate was washed for 3 times. 100 μL HRP was added into each well and the reaction was held at room temperature for 1 h. 100 μL TMB substrate was added into each well and kept in dark at room temperature for 15 min. 100 μL stop solution was added to each well, mixed gently to stop the reaction. OD values at 450 nm were read in 5 mins.

2.2.3 Results

Origin® software was used to plot the logarithm values of different concentrations against log OD values. According to the standard curve for determining the concentration of the samples in the 96-well plate, the concentration of recombinant G-CSF or YPEG-G-CSF in the samples was calculated by linear regression, and the serum concentration was obtained after calibration by the dilution factors.

2.3 Statistical Methods and Estimation of Pharmacokinetic Parameters

Figure 12:
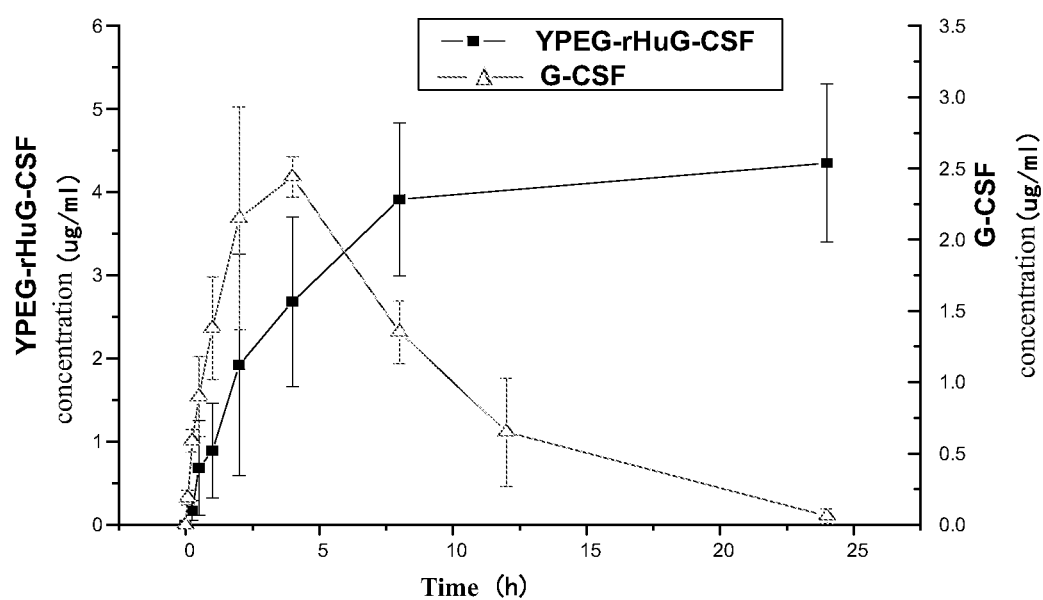
FIG. 12 shows the comparison of pharmacokinetic curves of PEG-GCSF and G-CSF.

The pharmacokinetic parameters were calculated by Rosenblueth method of non compartment model, and the software used was version 3P97. Comparison of the data of the same monkey was performed by Student's paired t-test, and comparison of the data of different monkeys was performed by t-test, and in both comparisons the calculation was performed by the statistical software provided by Microsoft Office Excel (version XP). The experimental data were processed by Origin® software to obtain the regression equation and relevant statistical parameters. The comparison of pharmacokinetic curves was shown in FIG. 12.

After injecting 300 μg/kg of YPEG-rHuG-CSF subcutaneously into cynomolgus monkeys, the serum YPEG-rHuG-CSF concentration reached its peak after 8~24 h, and $C_{max}$ was 4.53±0.86. Terminal half-life was 77.55±0.34 h, MRT was 95.03±14.51 h. $AUC_{(0-480\ h)}$ was 534.75±155.28 μg·h·mL$^{-1}$; $AUC_{(0-\infty)}$ was 539.27±158.32 μg·h·mL$^{-1}$. The average clearance rate was 0.60±0.20 mL·kg$^{-1}$·h$^{-1}$, substantially exhibited the characteristics of linear pharmacokinetics.

After single subcutaneous injection of 300 μg/kg G-CSF, $C_{max}$ was 2.49±0.20 μg·h·mL$^{-1}$, $AUC_{(0-24\ h)}$ was 23.07±2.93 μg·h·mL$^{-1}$, clearance rate was 12.95±1.95 mL·kg$^{-1}$·h$^{-1}$, terminal half-life was 4.00±1.44 h, MRT was 6.48±1.35 h, and $V_{SS}$ was 72.53±18.86 mL·kg$^{-1}$. The result indicated that the pharmacokinetic characteristics of YPEG-G-CSF were greatly different that of G-CSF in cynomolgus monkeys, and the YPEG modification of G-CSF resulted in the obvious reduction of the elimination rate constant, clearance rate and apparent volume of distribution and in prolonged MRT and terminal half-life (77.55±0.34 h vs 4.00±1.44 h)

---

We claim:

1. A Y-shaped PEGylated granulocyte colony stimulating factor (G-CSF) which is a compound of formula (I):

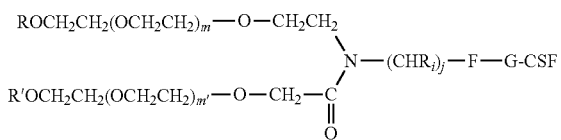

wherein
R and R' are independently low molecular weight alkyl;
m and m' are, independently of each other, an integer which denotes the degree of polymerization;
$R_i$ is H, substituted or unsubstituted $C_1$-$C_{12}$ alkyl group, substituted aryl, aralkyl, or heteroalkyl;
j is an integer of 1-12;
F is a terminal group which is a hydroxyl group, a carboxyl group, an ester group, acyl chloride, hydrazide, maleimide, or pyridine disulfide, wherein F is capable of reacting with an amino group on G-CSF to form a covalent bond, wherein the Y-shaped PEG is conjugated with the side chain ϵ-amino group of a Lysine (Lys) residue in said G-CSF at position 17 of SEQ ID NO: 1.

2. The Y-shaped PEGylated G-CSF of claim 1, which is a compound formula (II):

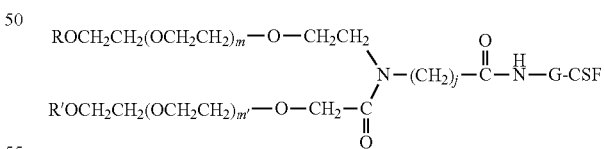

wherein
both R and R' are methyl;
j is an integer between 1-12;
m=m' and m+m' is an integer between 600 to 1500, endpoints inclusive.

3. The Y-shaped PEGylated G-CSF of claim 2, wherein the average total molecular weight of the PEG is from about 10000 to about 60000 Daltons.

4. The Y-shaped PEGylated G-CSF of claim 2, wherein the G-CSF is extracted from a natural source or obtained through recombinant biotechnology.

5. A method for treating a disease in a subject in need of G-CSF treatment, comprising administering in said subject an effective amount of the Y-shaped PEGylated G-CSF of claim 2.

6. A method for preparing and purifying the Y-shaped PEGylated G-CSF of claim 2, comprising:
(a) mixing a Y-shaped branched PEG of formula (III) with G-CSF in the ratio of protein:PEG=1:6 (mass ratio), Formula III

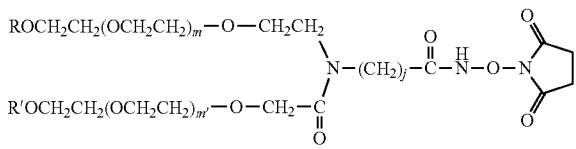

wherein both R and R' are methyl; j is an integer between 1-12;
m=m' and m+m' is an integer between 600 to 1500, endpoints inclusive;
(b) reacting said Y-shaped branched PEG of Formula III and said G-CSF at 4° C. to obtain the Y-shaped PEGylated G-CSF; and
(c) diluting the reacting mixture with 10 mM NaAc/HAc pH4.0, and loading the diluted mixture onto a cationic ion exchange column equilibrated with 10 mM NaAc/HAc pH 4.0; eluting with 10 mM NaAc/HAc+NaCl 160 mM pH4.0 buffer gradient, collecting the fourth peak, removing macromolecular polymers by a Sephacryl S-400HR column equilibrated with 10 mM sodium phosphate buffer pH 7.0, and collecting the eluent from the active peak to obtain the Y-shaped PEGylated G-CSF modified at position K17.

7. The Y-shaped PEGylated G-CSF of claim 1, wherein the R and R' are independently methyl.

8. The Y-shaped PEGylated G-CSF of claim 1, wherein m+m' is from 600 to 1500.

9. The Y-shaped PEGylated G-CSF of claim 3, wherein the average total molecular weight of the PEG is about 40000±4000 Daltons.

10. The Y-shaped PEGylated G-CSF of claim 4, wherein the G-CSF is obtained from recombinant biotechnology and comprises the sequence set forth in SEQ ID NO: 1.

11. The compound of Formula I of claim 1, consisting of a conjugation of said Y-shaped PEG with the side chain ε-amino group of a Lysine (Lys) residue in said G-CSF at position 17 of SEQ ID NO: 1.

12. The method according to claim 5, wherein the disease in need of G-CSF treatment is granulocytopenia induced by severe infection, leukemia, stem cell transplantation, or chemotherapy of malignant solid tumor.

* * * * *